(12) United States Patent
Aboutalebi (10) Patent No.: US 10,705,486 B2
(45) Date of Patent: Jul. 7, 2020

(54) MAGIC GLUCO-WRIST WATCH (MGW)

(71) Applicant: Zahra Aboutalebi, Tehran (IR)

(72) Inventor: Zahra Aboutalebi, Tehran (IR)

( * ) Notice: Subject to any disclaimer, the term of this patent is extended or adjusted under 35 U.S.C. 154(b) by 917 days.

(21) Appl. No.: 14/880,233

(22) Filed: Oct. 11, 2015

(65) Prior Publication Data

US 2017/0102673 A1    Apr. 13, 2017

(51) Int. Cl.
| | | |
|---|---|---|
| *G04G 21/02* | (2010.01) | |
| *G01N 33/487* | (2006.01) | |
| *G01N 33/49* | (2006.01) | |
| *A61B 5/145* | (2006.01) | |

(52) U.S. Cl.
CPC ....... *G04G 21/025* (2013.01); *G01N 33/4875* (2013.01); *G01N 33/49* (2013.01); *A61B 5/14532* (2013.01); *A61M 2230/201* (2013.01)

(58) Field of Classification Search
CPC ......... A61M 2230/201; A61B 5/14532; A61B 5/6848
USPC ........ 600/300, 309, 573, 583, 584; 606/181, 606/182
See application file for complete search history.

(56) References Cited

U.S. PATENT DOCUMENTS

| | | | | |
|---|---|---|---|---|
| 5,458,140 A | * | 10/1995 | Eppstein | A61B 5/14514 600/573 |
| 5,505,212 A | * | 4/1996 | Keljmann | A61B 5/150022 600/573 |
| 6,042,595 A | | 3/2000 | Morita | |
| 6,059,736 A | * | 5/2000 | Tapper | A61N 1/0436 600/573 |
| 6,793,633 B2 | * | 9/2004 | Douglas | A61B 5/14532 600/583 |
| 6,852,119 B1 | | 2/2005 | Abulhaj et al. | |
| 7,047,070 B2 | * | 5/2006 | Wilkinson | A61B 17/205 600/573 |
| 7,258,673 B2 | * | 8/2007 | Racchini | A61B 5/14532 600/583 |
| 7,377,904 B2 | * | 5/2008 | Conway | A61B 5/15146 600/583 |
| 7,582,063 B2 | * | 9/2009 | Wurster | A61B 5/14532 600/583 |
| 7,879,058 B2 | | 2/2011 | Ikeda | |
| 7,942,831 B2 | * | 5/2011 | Sawa | A61B 5/14514 600/345 |
| 8,147,426 B2 | * | 4/2012 | Neel | A61B 5/150503 221/25 |
| 8,641,644 B2 | * | 2/2014 | Freeman | A61B 5/14532 600/584 |
| 8,787,006 B2 | | 7/2014 | Golko et al. | |
| 8,870,903 B2 | * | 10/2014 | LeVaughn | A61B 5/1411 604/218 |
| 2002/0087056 A1 | * | 7/2002 | Aceti | A61B 5/14532 600/309 |

(Continued)

*Primary Examiner* — May A Abouelela
(74) *Attorney, Agent, or Firm* — Azadeh Saidi (57) ABSTRACT

The Magic Gluco Wrist Watch (MGW) is a time wrist watch with a capability to measure the blood glucose level. The fix watch clasp plays a role of a lancing device, and is attached to the end of a left strap of the MGW. The movement of a holding member from the left strap to a right strap causes new electric current test strip to be driven in to the test strip port. A test strip port is located in the lug. By opening the valve, the MGW turns from time watch into a blood glucose meter.

20 Claims, 10 Drawing Sheets

(56) References Cited

U.S. PATENT DOCUMENTS

| | | | | |
|---|---|---|---|---|
| 2004/0138588 A1* | 7/2004 | Saikley | ............... | A61B 5/1411 600/583 |
| 2004/0230216 A1* | 11/2004 | Levaughn | ............ | A61B 5/1411 606/181 |
| 2006/0235454 A1* | 10/2006 | LeVaughn | ........ | A61B 5/150022 606/181 |
| 2006/0276724 A1* | 12/2006 | Freeman | ............ | A61B 5/14532 600/583 |
| 2007/0179404 A1* | 8/2007 | Escutia | ............... | A61B 5/1411 600/583 |
| 2008/0243159 A1* | 10/2008 | Schraga | ............... | A61B 5/1411 606/167 |
| 2009/0326355 A1* | 12/2009 | Brenneman | ........ | A61B 5/14532 600/347 |
| 2013/0274568 A1* | 10/2013 | Escutia | ............... | A61B 5/1411 600/309 |
| 2015/0342509 A1* | 12/2015 | Peeters | ............ | A61B 5/150099 600/573 |

\* cited by examiner

MAGIC GLUCO-WRIST WATCH (MGW)

FIELD OF THE INVENTION

The invention relates to a blood glucose meter, in the shape of a wristwatch, which combines a lancing device, a time measuring device and a hollow watch strap to hold a plenty of electric current test strips. In this invention the lancing device is designed to fasten the watch strap.

BACKGROUND

According to the statistics of the International Diabetes Federation (IDF), one of the most prevalent metabolic disorders is diabetes. Because of this chronic disease, the body cannot produce enough insulin or absorb it efficiently. Nowadays, in average, one out of six people is diabetic. Recent studies show that one, by controlling blood glucose level, injecting timely proportionate insulin, exercising regularly and having a healthy dietary program, can prevent diabetes repercussions. So measuring blood glucose level before and after food and before going to sleep, on a daily basis, is a key factor for diabetics to live healthy without diabetes side effects.

Therefore due to increasing number of diabetics and increasing demand in the market for medical instruments to control the disease, there was a need to overcome the shortcomings of older glucose measuring models.

Today most of the glucometers in the market comprise of three separate components:
Screen, lancet, and strip, packed together in a small bag. Because of different separate components, these kinds of glucometers are not efficient in all situations especially in outdoor situations.

It is noteworthy that most of the type 1 diabetics (dependent on insulin) are children or youth who are very active and usually stay outdoor in schools or universities during the day. For example when a diabetic is playing or driving car or is walking on the street in rush hour, cannot easily open the bag and use several components to measure his/her blood glucose.

Because of these shortcomings, the diabetics who are dependent on insulin cannot control the fluctuations of their blood glucose level regularly. Therefore "accessibility" and "user friendly" are the most important features of such a device to provide convenience for diabetics to control their blood glucose every time in every situation or in every location to mitigate any side effect of the disease in the future.

Diabetics dependent on Insulin (type 1) contrary to independent diabetics (type 2) normally face with blood glucose level fluctuations during the day. So multiple blood testing is necessary for them to control these fluctuations as soon as possible. Therefore "easy to use" feature of device and "having access" to it in every situation is very vital for the users.

A diagnostic apparatus of this type is known from U.S. 2013/0274568 A1, an arrangement comprises housing multiple needles. Each needle has an inner passageway or lumen, an analyst quantification member that comprise an assay pad is provided in communication with the lumen of the needle, can receive a sample of blood produced by the piercing of the user's skin with the needle. Each needle pierces the user's skin by the torsional spring elements that are mounted to triggering member. The plurality of components of this device such as plurality of needles and actuators indicates the complexity of the system, which causes the manufacturing and assembling of device becomes more sophisticated and expensive. Also changing the used needles and assay pads couldn't be user friendly.

U.S 2014/0114160A1 shows a blood testing apparatus which includes a laser source configured to produce a wound from which blood flows for measuring its glucose level. This apparatus has also a plenty of components which make it complex and big. These features altogether could lessen the attractiveness of the device and increase its manufacturing cost.

SUMMARY OF THE INVENTION

Regarding the needs of diabetics for multiple testing and the difficulties they face to maintain the balance of their blood glucose level, in this invention a device is designed in a way to be wearable and being attached to the user, to be as compact and integrated as possible, and to be user friendly.

I decided to design the device in the shape of a wristwatch and to use each part of it as a component of the conventional glucometer. Thus each part of the Magic Gluco Wrist Watch (MGW) has multifunction. For example the glucowatch strap beside the function of fastening the MGW around the wrist of the user, also has the function of holding the electric current test strips and the lancing device. The other competitive advantage of this invention compared to other devices is its simplicity.

MGW has less components, is easy to assemble and to manufacture and easy to repair. This invention despite to other new-designed devices is a mechanical device and doesn't include any electromechanical components that renders the device complex and not easy to use, which causes complexity rather than simplicity of the device.

In this invention, MGW is a portable device which provides a simple and fast method for rapid monitoring of the blood glucose level by utilizing a blood sample from the user's fingertip. The MGW is a smart digital wristwatch capable of displaying time, date, location of a user, weather forecast, heart rate, body temperature, emails as well as any information being transmitted to the smart wristwatch via Bluthooth™, WIFI, or home internet or any user data being transmitted via any communication protocols through a transmitting means such as a mobile smart phone, any type of computer or laptop, received by a receiving means located inside the watch (Incorporated by reference to U.S. Pat. No. 8,787,006 Golko et al). Where the user can enter any kind of data via a touch screen display and interact with the data received to the wristwatch or smart phone or computer or laptop as well send glucose measurement date saved on a memory inside the watch when needed, either manually or automatically.

The user can utilize programs and softwares created for diabetic patients in order to send any glucose measurement data continuously or during specific time intervals or at one point to his/her smart phone, laptop or any computer such as a physician's office.

All the data processing and analyzing is performed via a watch processing mean (not shown, but well known in the art of smart watches and smart phones). The watch comprises necessary transmitter, receiver means in order to communicate and receive data as well as a CPU designed to control and run the whole system including the watch processing mean and glucose measurement unit (data received by test strips, glucose level, insulin intake and so on). The watch comprises two alarm systems one used for the wrist watch and works as an alarm clock and the other alarm is for alerting the user when his/her insulin level falls below a certain level. The alarm system can also send signal and data to the smart phone, laptop and computer and also to the physician's office as well as other health providing organizations such as hospitals and health centers. The alarm can be a sound, light (flashing or pulsating) or vibrating and any combination of the aforementioned.

Usually diabetics for measuring their blood glucose level, need three separate components i.e. lancet device, test strip and glucose meter. One of the features and advantages of this invention is that it is very compact (three in one) device, simple and available in usage (in every place and situation). MGW is designed to be handheld and wearable in the form of a wristwatch and always is attached to the user. Because of this feature, the process of blood glucose monitoring becomes less time consuming and very user friendly.

In each blood glucose monitoring, there is no need to insert a new electric current test strip into the test strip holder and to discard it after each measurement.

In another aspect of this invention, the feature of "not to attract the attention of others" is secured. Every diabetic likes to preserve his/her privacy during measuring the blood glucose level. So shaping the glucose meter as a wristwatch makes this "control" very convenient and easy and not attractive to others. It is also noteworthy that each components of the MGW has a specific function and is playing a role in the monitoring process. For example the strap of the MGW is a holder of the strips, and the fix watch clasp functions as a lancing device and so on. This feature enables the design to become as compact as possible.

Another remarkable aspect of this invention is that it does not expel the used electric current test strip out of the MGW, because the right strap of the MGW holds the used electric current test strip.

LIST OF PARTS

Below is list of all the components of MGW as fully disclosed in detailed description:
4 Lug/main body
5 Valve (push to slide door)
6 Holding member
7 Lancing device
8 Toggle button
9 Sampling hole
10 Lance button
11 Sampling area
12 Test strip
13 Curved shape
14 Left strap
15 Right strap
17 Jag member intervals
18 Stopper
19 Spring-Wise jags
20 Frame
21 Receiving port
22 Docket
23 Docketing roof
24 Tip of test strips
25 Magnetic layer
26 Cap
27 Silica gel packet
28 Watch clasps
29 Watch control buttons
30 Display screen
31 Opening/strip window
40 End of test strip

DETAILED DESCRIPTION

The MGW, as a Smart Wristwatch, can be connected to the internet (IOT) and be equipped with GPS, wireless and Bluetooth. Taking into account that in case of hypoglycemia the patient faces the high risk of convulsion, so being tracked by his/her doctor or the emergency room is very crucial. While the patient is driving or exercising and the MGW is connected to the internet the data of blood testing is transferred immediately to the emergency room to take care of him/her timely. Another important feature of the MGW is it is capability to work as a CGM (Continuous Glucose Monitoring) device.

The importance of CGM (incorporated by reference from Jin et al, 2004/186365) method is that blood glucose meters only provide a number for a single point in time, while CGM gives dynamic information and showing the fluctuation of the glucose level.

Usually CGM devices comprises of three parts:
1—A small sensor which is placed underneath the skin to measure glucose levels.
2—A transmitter which is fastened on top of the sensor and sends data to the receiver wirelessly.
3—A receiver that shows glucose trends (being normal or going up or down) in different colors.

Figure 2A:
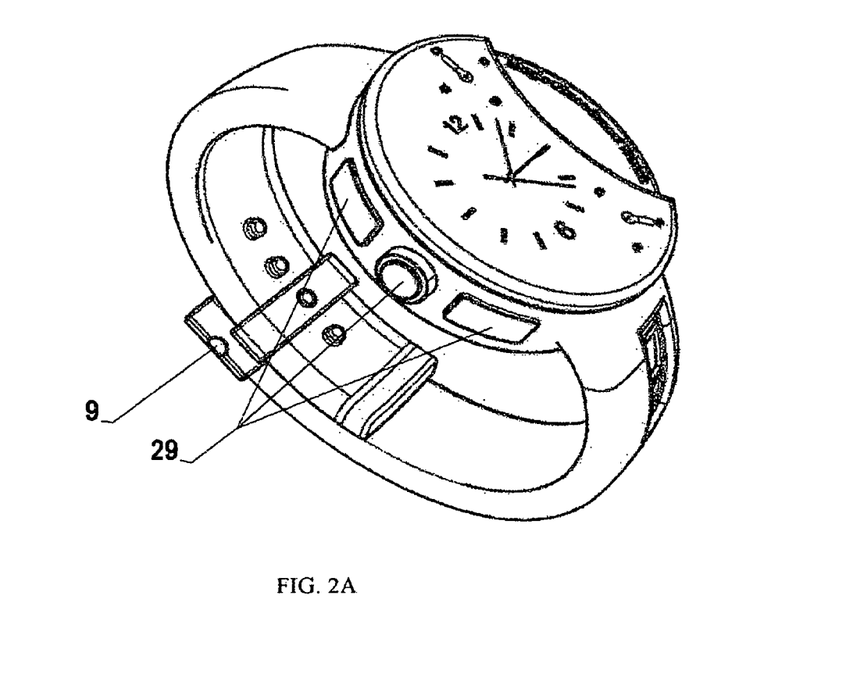
FIG. 2(a)-(b) shows the different perspective views of the lancing device.

Therefore according to FIG. 2(a) lug 4 of the MGW can also function as a receiver. Lug 4 encompasses the whole body of the wrist watch including the straps.

All CGM devices need calibration 2 or 4 times a day by testing blood glucose level manually. While the left strap 14 of MGW contains the electric current test strips 12, were lug 4 works as a receiver, so the user can easily use the MGW as a manual blood glucose meter and then can instantly calibrate the receiver (lug 4) of the MGW.

In this way screen 30 of MGW can show information such as the real-time interstitial fluid glucose level measured by a sensor (not shown. However glucose monitoring sensors are well known in the art) and draw the glucose trend and blood glucose measurements. Buttons 29 can be used to adjust the time or perform the receiver's actions.

As a conclusion installing a receiver in lug 4 and matching and configuring it with the small sensor (not shown) and its related transmitter (incorporated by reference Jun et al.), the user will have a compact device including a manual meter and a continuous glucose monitoring (CGM) device which is highly portable, user friendly and exactly tailored to the diverse needs of a diabetic.

The MGW can be waterproof and radiation proof. In particular the straps of the MGW can be made of plastic silicon or similar materials in order to be completely flexible and water proof.

Figure 1A:
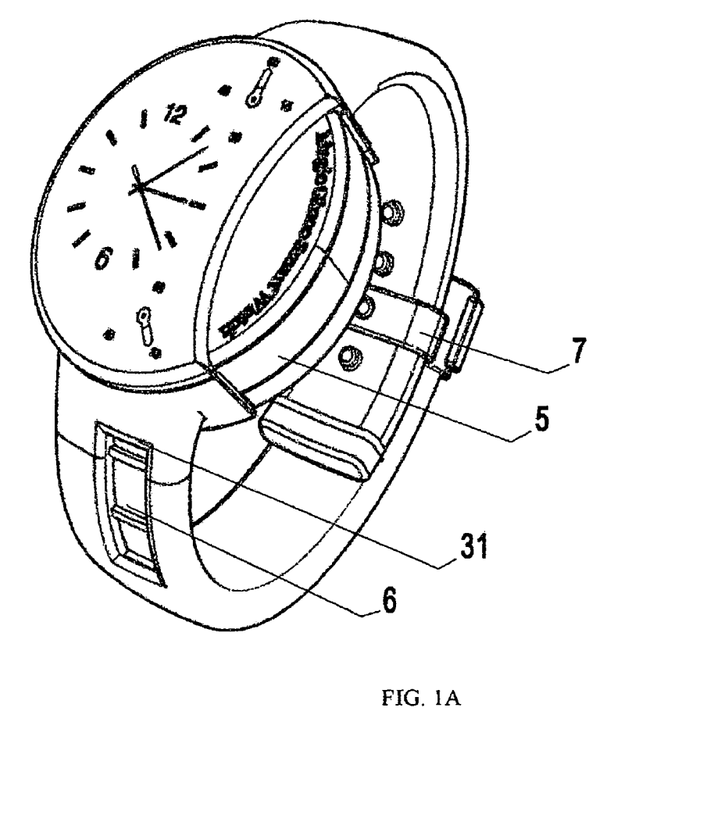
FIG. 1(A) displays a perspective view of MGW showing a watch face in a closed and shot off setting.

FIG. 1(a) displays a perspective view of lug 4 with screen 30 and the closed valve/push to slide open 5 of lug 4. When door 5 is closed the MGW is a time wristwatch and when the user opens the door 5 the MGW turns into a blood glucose wristwatch. Strap hole/opening 31 is made inside the left strap 14 through which the holding member 6 is pushed to move forward, in order to place the new electric current test strip 12 in its port.

Figure 2B:
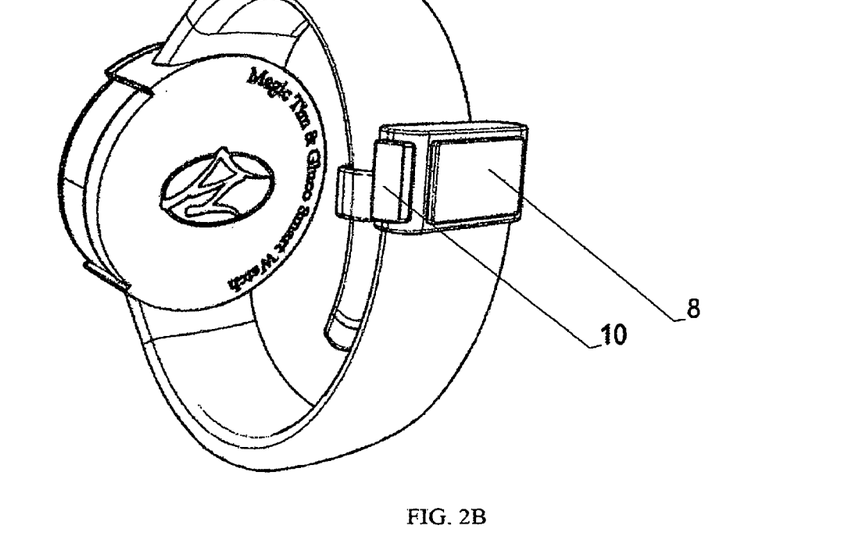

FIG. 2(a)-(b) shows straps 14 and 15 are fastened to each other by lancing device 7. During blood sampling the user pushes back toggle button 8 to set the lancing device 7, then puts his/her finger on the sampling hole 9. By pressing "lance button" 10, needle (not shown) is triggered and pierces the skin surface of the user's fingertip.

It is noteworthy that the sampling hole 9 can have a cover like a camera lens' cover. By pushing a toggle button 8, a cover of the sampling hole 9 becomes open.

Lancing device 7 can have a component named "lancet drum" which contains multiple needles (not shown). Every time the lancing device 7 is used, the lancet drum is rotated and a new needle is loaded for the next test.

In another embodiment the lancing device 7 by reference to U.S. Pat. No. 6,852,119 B1, incorporates only a single needle, which can be replaced with a new one manually.

In another embodiment, the packing of the needle can be located in the strap of the MGW. By each test a new needle can enter the lancing device 7 from the strap, and when it is used it can be easily discarded. In another embodiment the lancing device can hold multiple sterilized lancing needles located inside the lancing device and being loaded similar to a gun and a round of bullet mechanism where, the used needle can be either discarded by means of a trigger located on a side of the lancing device and or being discarded inside in the lancing device, where a lancing needle holder rotates after each use, pulling in the used lancet and loading a new lancet ready to be pushed out for another glucose measurement when needed.

Figure 1B:
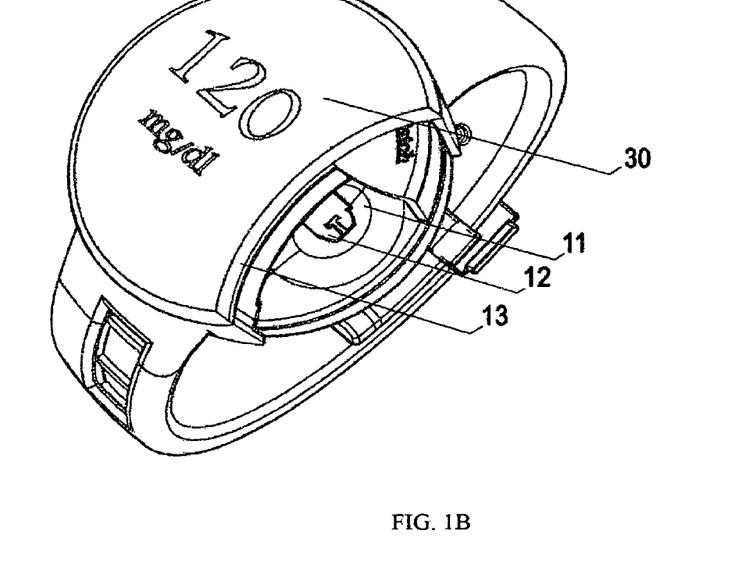
FIG. 1(b) displays MGW when changed into a glucose measuring face, with valve/push to slide door open, allowing access to the glucose measuring system.

According to FIG. 1(b), after getting blood sample, the user opens door 5 by pressing valve lock (not shown) in the direction of the arrow counter clockwise lug 4 which changes the time wristwatch into blood glucose wristwatch. By pushing up holding member 6 through the strap opening 31 on the left strap 14, a new electric current test strip 12 will be placed on its port (not shown). Due to the curve shape 13 of the lug 4 the end 40 of electric current test strip 12 in sampling area 11 becomes accessible.

Then by touching the end 40 of electric current test strip 12 with the wounded fingertip, the blood sample is absorbed and finally within few seconds the result of the blood glucose level is shown on lug 4 of screen 30. After ending this process there is no need to extract the used electric current test strip 12 because in the next measuring it is pushed forward through the right strap 15 and it is replaced with a new electric current test strip 12. By closing door 5 the MGW is changed again from glucose meter into time wristwatch.

Figure 4:
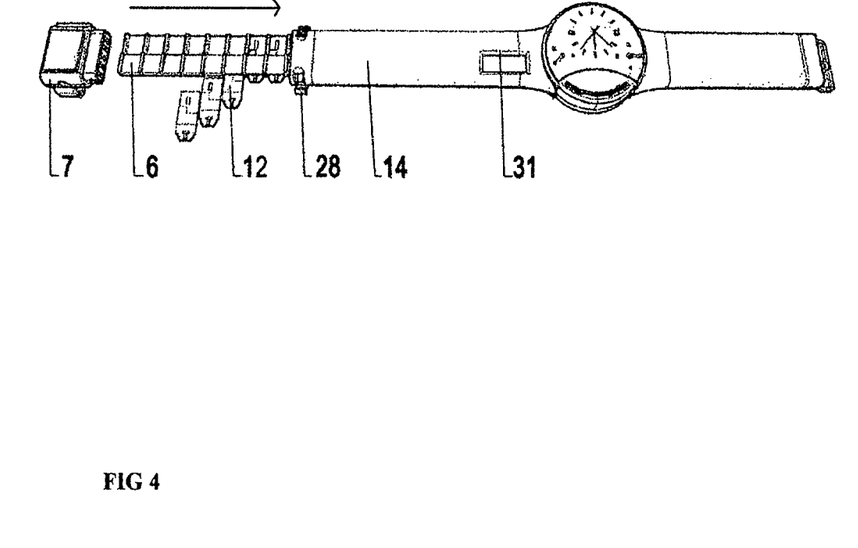
FIG. 4 shows the exploded view of the wrist-watch strap and depicts loading the new electric current test strips on the holding member and the passage of them through the left strap in order to locate the new electric current test strip in its port.

FIG. 4 shows the position of the electric current test strips 12 on the holding member 6 which contains 12 to 14 electric current test strips. This holding member 6 as is shown in FIG. 4 can easily move within the straps, from left strap 14 to right strap 15. By pulling out the lancing device 7 from strap 14, and pushing in the holding member 6 inside strap 14, the holding member 6 can move and be pushed in the left strap 14.

Figure 3A:
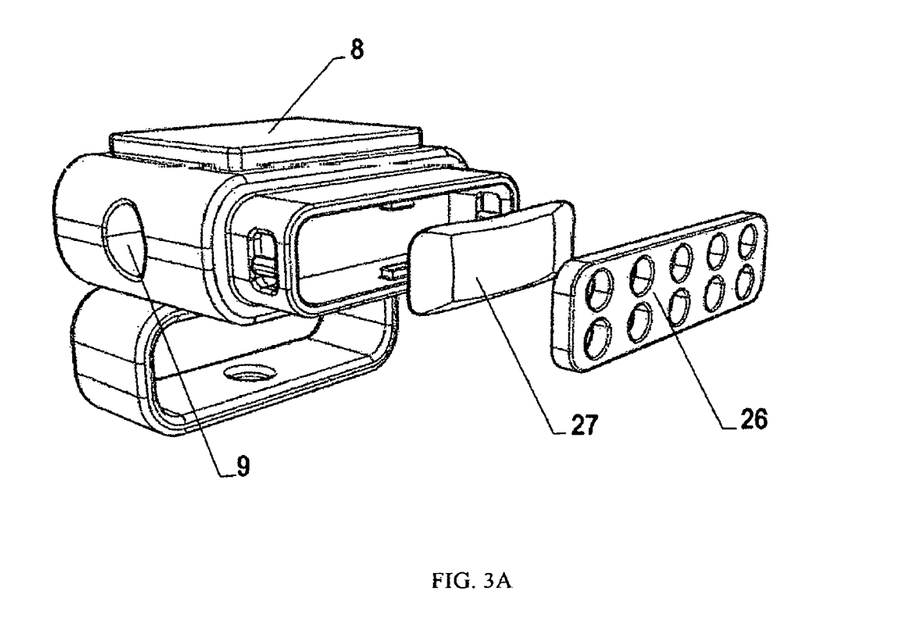
FIG. 3(a)-(b) shows the location of the silica gel inside of the lancing device.
Figure 3B:
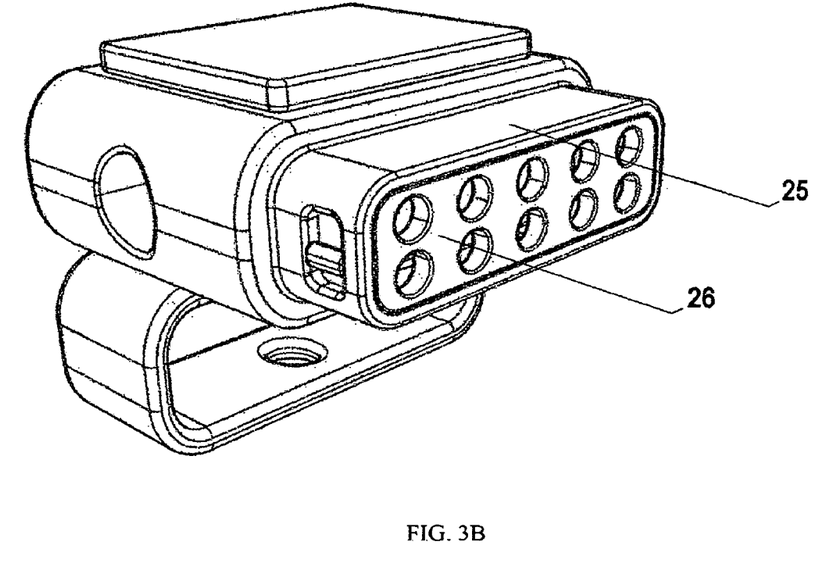

As is visible in FIGS. 3(a)-(b) after pulling out the lancing device 7 from the left strap 14, by pulling out cap 26 of the lancing device 7, a silica gel packet 27 will be placed inside the lancing device 7 to keep the electric current test strips 12 dry.

Figure 5A:
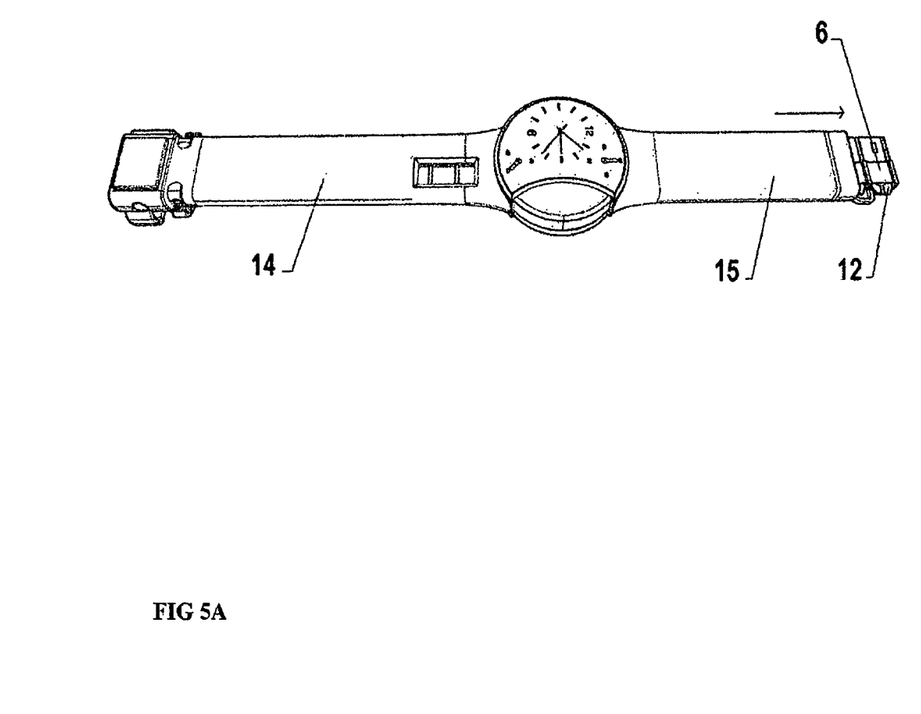
FIGS. 5(a)-(b) shows the exit of "holding member" and the used electric current test strips, out of the right strap.

FIG. 5(a) shows how holding member 6, which contains the used electric current test strips 12, can be extracted and removed from the right strap 15.

Figure 5B:
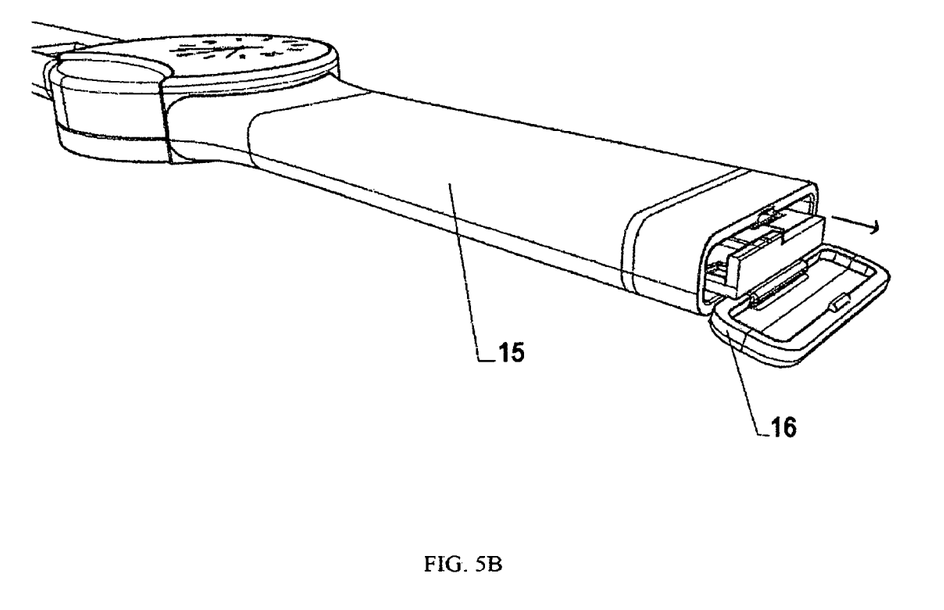

According to the FIG. 5(b) by opening the extract cap 16 of the right strap 15, the tip of the holding member 6 exiting from right strap 15, becomes accessible. By holding this tip, the holding member 6 can be completely removed from the right strap 15.

Figure 6:
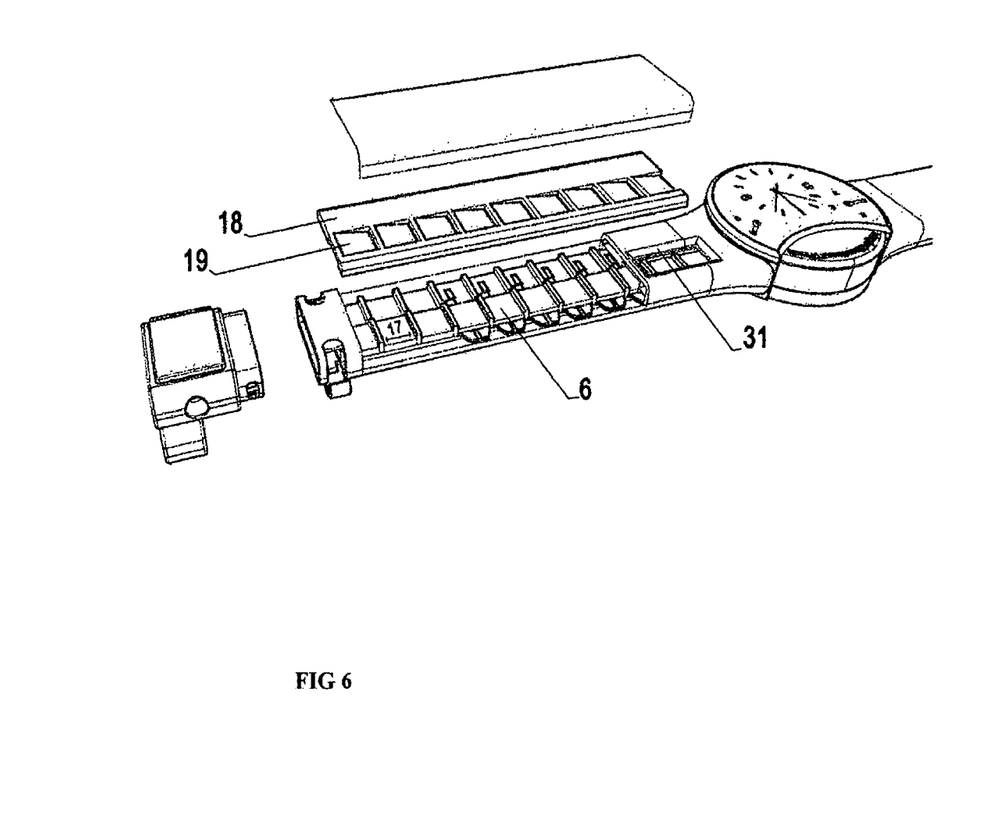
FIG. 6 shows the exploded view of the left strap of the MGW.

FIG. 6 shows the exploding view of the left strap 14. Stopper 18, which has spring-wise jags 19, is positioned above the holding member 6 inside the strap 15. When the stopper 18 is fixed above the holding member 6, each jag 19 stops the holding member 6 to move back from right to left.

As is visible in FIG. 6, opening 31 is made on the left strap 14 in order to push forward the holding member 6 through lug 4 and the right strap 15. This movement takes place strip by strip, due to the function of the stopper 18. Because the spring-wise jags 19 of stopper 18 falls between the jags 17 of the holding member 6. A counter can be implemented next to opening 31 in order to display the number of test strips used, or to display the number of test strips remaining inside lug 4. Jag intervals 17 may also have numbers or letters hacked and marked on them so that it can be clearly shown through opening 31, informing the user about the number of test strips used or remaining. It is obvious that the letters or numbers can be in ascending or descending order, giving different information (number of test strips used or number of test strips remaining respectively).

Figure 7:
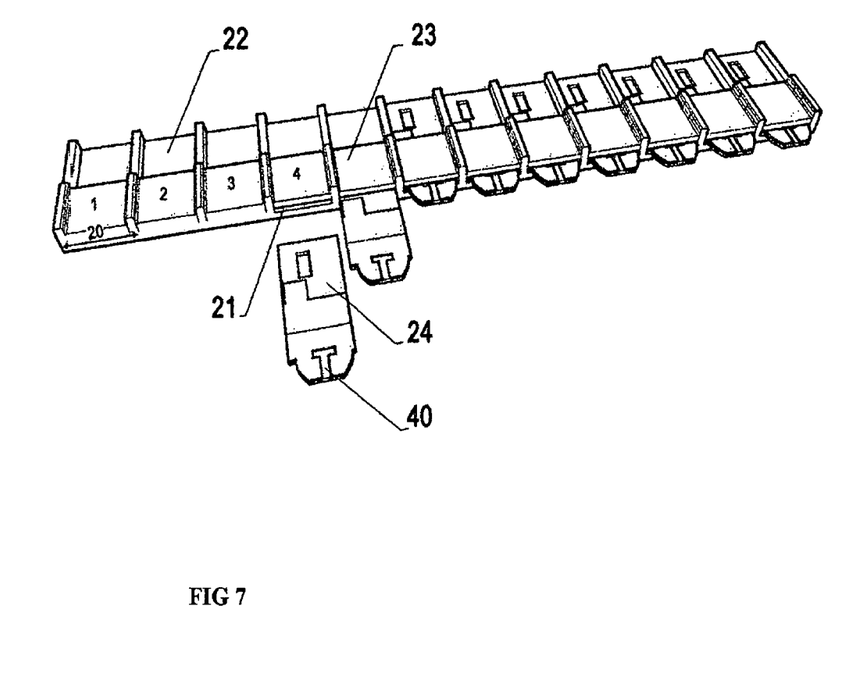
FIG. 7 shows the holding member and the position of electric current test strip on it.

According to FIG. 7, the holding member 6 shows 12-14 frames 20. Frame numbers 1, 2 and 3 do not contain any electric current test strip 12. But each of the frame numbers 4 to 12, have an opening (receiving port) 21 through which the electric current test strips 12 can be placed inside the holding member 6.

The reason that frame numbers 1, 2 and 3 do not contain any electric current test strip 12 is that the distance between strap hole opening 31 and the test strip port (not shown) or sampling area 11 is exactly the same as the length of these three frames and therefore the holding member 6 cannot be pushed forward any more within opening 31; and even if those frames did contain electric current test strip 12, those electric current test strip 12 could not be placed on the test strip port (not shown) or sampling area 11.

Figure 8:
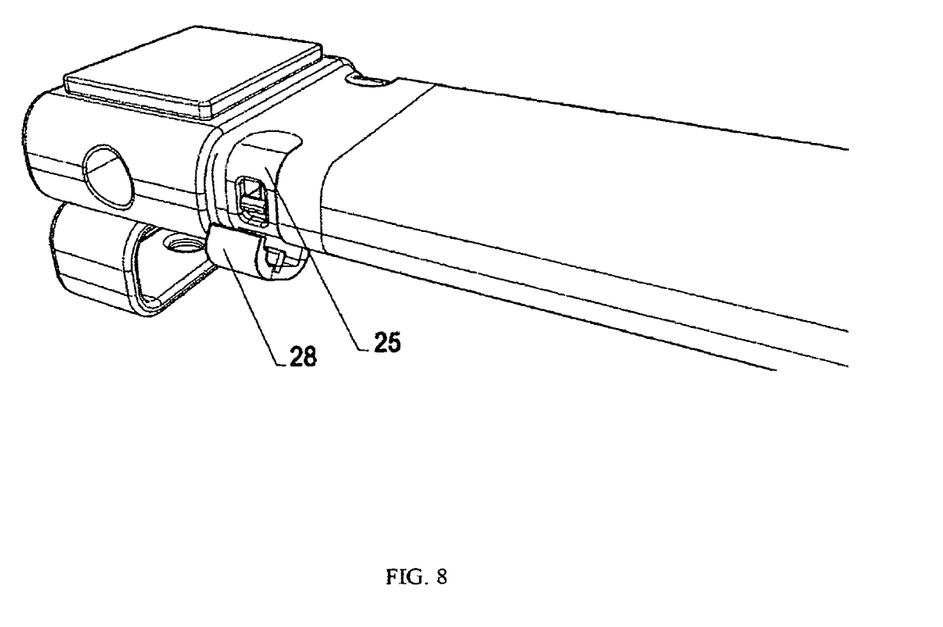
FIG. 8 shows how the lancing device is fastened tightly to the left strap.

As is shown in FIG. 8 when the electric current test strip 12 is placed inside the holding member 6, a beginning (tip) 24 of the electric current test strip 12 which has electrodes will be located on docket 22 of holding member 6 (in docket 22 of holding member 6 the test strip 12 is not covered), in order to be in touch with the measuring contact (not shown) in the test strip port (not shown).

Two types of holding member 6 can be produced. One type is a disposable holding member which should be discarded after using its last electric current test strip 12. The other type is that the holding member can be used as a prepackaged test strip cartridge, where the electric current test strips 12 are already loaded. In a different embodiment holding member 6 can be loaded manually with test strip 12.

As shown in FIG. 8 the left strap 14 is connected to the lancing device 7 by a magnetic layer 25. In addition to this magnetic 25 layer, for the safety and durability of the connection, two clasps 28 fasten the left strap 14 to the lancing device 7.

It is understood that the above described description and drawings are illustration of the present invention and that changes may be made in materials, lancing device, triggers, closing and stopping means and loading mechanism without departing from the scope of the present invention as defined in the following claims:

The invention claimed is:

1. A Magic Gluco Wrist Watch (MGW) apparatus for measuring and monitoring glucose level comprising: a wristwatch comprising a main body/lug, a left and right watch straps each having a left and right slot nestled inside, extending along a length of left and right strap bodies; a display screen located on top of said wristwatch; at least one watch clasp; a holding member, multiple new test strips, at least one lancing device, wherein said test strips are located and move inside said left and right strap bodies; an arced shaped push to slide open door covering said multiple new test strips, wherein when said door is in a closed setting said display screen has a full circular shape/design and wherein when said door is open display screen has a crescent design, said push to slide open door is slid open with a counter clockwise motion and is slid shut and closed with a clockwise motion; said left strap having an opening/window displaying the holding member and at least two holding member jags, wherein said holding member comprises multiple frames/cartridges.

2. The apparatus of claim 1, wherein used test strips are held inside said right strap body and is not discarded after each use, when all of said new multiple test strips are completely used the used test strips are removed from said right watch strap through said right slot.

3. The apparatus of claim 2, wherein said wristwatch is a smart digital watch where time, date, location, weather forecast, emails or/and user data transmitted via communication protocols from a smart phone or computer to a laptop to said wristwatch and received via a receiver inside said main body, the user data is displayed on said display screen of a watch interface; and the monitored glucose level, time or other health related data are displayed on said display screen of a glucose monitoring interface; wherein said watch interface and glucose monitoring interface are interchangeable, and wherein said watch interface is on display at all times and wherein glucose monitoring interface is active when said push to slide door is slid open.

4. The apparatus of claim 3, wherein said display is touchscreen and data is entered and sent through said transmitting protocol via said wristwatch including said monitored glucose level.

5. The apparatus of claim 4 wherein said glucose measurement data is saved in a memory located inside said main body and is transmitted to said smart phone and/or laptop and/or computer and/or physician's office or emergency room, wherein said transmission is initiated manually or automatically at certain time intervals and/or continuously and/or as needed; and wherein said glucose measurement data is calculated and displayed based on programs run by a processing unit located inside said wristwatch.

6. The apparatus of claim 5, wherein said MGW comprises at least one alarm system, comprising at least one flashing or pulsating light, vibration and/or sound and/or any combination thereof, flashing and pulsating light and/or vibration; and wherein said alarm system is activated when the glucose level falls below a predetermined value saved in said memory.

7. The apparatus of claim 6, wherein said push to slide open door is locked at all times and is opened by pushing a release button of a child safety lock; and wherein one of said new multiple test strips is loaded on a sampling area that is located underneath said push to slide open door when said safety lock is released.

8. The apparatus of claim 7, wherein said holding member contains at least 12 to 14 test strips in a belt shaped setting, where said jags protruding from a surface of said holding member creating a ladder effect.

9. The apparatus of claim 8, wherein said jag comprise letters or numbers being displayed through a strap opening; wherein said letters and numbers are in ascending or descending order, displaying a number of said used test strips or a number of said new test strips remaining inside said left strap.

10. The apparatus of claim 9, wherein said slide door stays shut with at least one of: a magnetic force, and/or a push pin and/or a trigger and/or a spring and/or clasping structure.

11. The apparatus of claim 10, wherein said holding member is configured to moves from and inside said left strap to and inside said right strap through their respective left and right slaps, wherein when a blood sample is taken and said door is slid shut and closed, by releasing said child safety lock embedded inside said lancing device and left strap, said holding member can move through said left strap towards said right strap allowing said used test strip to be pushed and discarded inside said right strap by pushing said protruding jags up towards said display screen, and one of said multiple new test strips is placed/lunched on said sampling area.

12. The apparatus of claim 10, wherein when said door is slid open, one of said multiple new test strips are lunched and placed on said sampling area by pulling out said lancing device from said left strap, releasing a stop mechanism from locking in said holding member in place and said used test strip is discarded inside said right strap by pushing said protruding jags up towards said display screen, and one of said new multiple test strip are placed/lunched on said sampling area.

13. The apparatus of claim 12, wherein said lancing device further comprises a cap, and a hollow compartment, wherein by pulling out said cap a silica gel packet is placed inside said lancing device hollow compartment in order to keep said new multiple test strips dry.

14. The apparatus of claim 13, wherein said right strap comprises an extract cap for removal of said holding member containing all of said used test strips, wherein a sterilized and prepackaged new set of holding member with respective said multiple new test strips are loaded inside said left test strip by releasing and removing said lancing device from an end of said left strap via multiple watch clasps.

15. The apparatus of claim 14, wherein said multiple watch clasps comprise fasteners, hooks, clips, press-studs, poppers and/or hook and eye configuration and respectively said lancing device comprises structure configured to match/mate with said fasteners, hooks, clips, press-studs, poppers and/or hook and eye configurations of said multiple watch clasps respectively for tightly and securely connecting and holding said lancing device to said left strap.

16. The apparatus of claim 15 further comprising a stopper part having spring-wise and/or reversed jags opposed to said holding member jags, locking with said holding member and preventing said holding member from moving, from right to left inside said left strap, said stopper provides one strip at a time movement of said new or used test strips.

17. The apparatus of claim 16, wherein said strap opening comprises a counter displaying number of said used test strips or number of said new test strips remaining inside said left strap.

18. The apparatus of claim 17, wherein each of said multiple frames/cartridges hold said new multiple test strips in place, and each of said multiple frames further comprises a docket where electrodes and electrical component of said new and/or used test strips are exposed to said MGW processing unit, and also comprises a receiving port having a docketing roof, through which said new test strips are loaded inside said holding member.

19. The apparatus of claim 18, wherein said right and left clasp are made of semi-rigid and/or rigid waterproof material, comprising silicon, plastic capable of sterilization and/or user friendly.

20. A method of using a Magic Gluco-wrist watch glucose measuring and monitoring apparats, comprising a wristwatch comprising a main body/lug, a left and right watch straps each having a left and right slot nestled inside, extending along a length of their respective left and right strap bodies; a display screen located on top of said wristwatch; at least one watch clasp; a holding member comprising multiple holding member jags; wherein multiple new test strips are located inside said holding member, at least one lancing device, wherein said multiple new test strips are located and move inside said left and right strap bodies; an arced shaped push to slide open door covering either one of said multiple new test strips and/or one used test strip, wherein said method comprises steps of: during a first time glucose measurement said lancing device is removed from said left strap by releasing a stop mechanism from locking in said holding member in place, and said holding member will move from said left strap towards said right strap by pushing up said holding member jags inside a strap opening, towards said display screen, loading one of said at least new test strips and after said first time use, by pushing said holding member jags upwards from said left strap towards said display screen said used test strip is moved from a sampling area located underneath said push to slide open door and lunches one said multiple new test strips on said sampling area; wherein by lunching one of said multiple test strips, a counter located next to said opening displays either a number of said used test strips or a number of said multiple new test strips remaining; wherein said holding member only move from said left strap towards said right strap; and wherein when all of said multiple new test strips are used, said holding member is extracted through said right strap by removing an extract cap located at an end of said right strap, wherein a stopper located on top of said holding member prevents said holding member from moving back inside said left strap and only allows single lunch of said multiple new test strips at a time; wherein during said glucose measurement said lancing device is set by pushing a toggle button, a sterilized and new lancet is triggered out from said lancing device when a lance button is activated is adapted to piercing a digit or skin placed on a sampling hole; wherein said push to slide open door is slid open by rotating said door in a counter clockwise direction, exposing one of said multiple new test strips on said sampling area where a blood sample is collected, then said display screen, displays calculated glucose data and will sound an alarm and communicates wirelessly, said data via an external laptop, computer, mobile phone and/or physician's office and/or emergency room, wherein said glucose measurement said door is closed by rotating said door in a clockwise direction; wherein said used test strips are held inside said right strap body and is not discarded after each use, and when all of said test strips are used, said holding member and all of said used test strips are discarded as a single unit and is replaced with a new prepackaged set comprising a new holding member with respective set of new test strips.

* * * * *